United States Patent
Sugiyama et al.

Patent Number: 5,883,285
Date of Patent: Mar. 16, 1999

[54] PROCESS FOR PRODUCTION OF THIOARYL COMPOUND

[75] Inventors: Tatsuo Sugiyama, Shizuoka-ken; Tadashi Nakayama, Tokyo, both of Japan

[73] Assignee: Ihara Chemical Industry Co., Ltd., Tokyo, Japan

[21] Appl. No.: 970,151

[22] Filed: Nov. 13, 1997

Related U.S. Application Data

[63] Continuation of Ser. No. 532,801, filed as PCT/JP95/00455 Mar. 17, 1995, Pat. No. 5,750,763.

[30] Foreign Application Priority Data

Mar. 17, 1994 [JP] Japan .................................. 6-072524

[51] Int. Cl.$^6$ .................................................. C07C 321/28
[52] U.S. Cl. ........................... 560/17; 564/192; 564/215
[58] Field of Search ..................... 564/192, 215; 560/17

[56] References Cited

U.S. PATENT DOCUMENTS

| | | | |
|---|---|---|---|
| 2,010,731 | 8/1935 | Lubbert . | |
| 2,026,629 | 1/1936 | Haddock . | |
| 3,116,321 | 12/1963 | Horn . | |
| 3,296,308 | 1/1967 | Walker . | |
| 5,248,822 | 9/1993 | Ohi .......................................... | 564/154 |

OTHER PUBLICATIONS

Derwent WPIDS accession no 90–278128 and Chemical Abstracts CA:114:61701 both are abs of JP02193961, Jan. 1989.

*Primary Examiner*—Paul J. Killos
*Assistant Examiner*—Jean F. Vollano
*Attorney, Agent, or Firm*—Oblon, Spivak, McClelland, Maier & Neustadt, P.C.

[57] ABSTRACT

The present invention provides:

a process for producing an alkali metal salt of an arylmercaptan compound, represented by general formula (3):

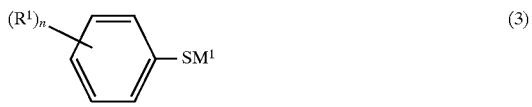

which process comprises reacting a disulfide compound represented by general formula:

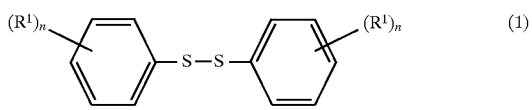

with a hydroxide of an alkali metal $M^1$ in the presence of a sulfur compound represented by general formula (2):

$$H_{(2-i)}S(M^1)_i \qquad (2)$$

a process for producing an alkoxycarbonylalkylthioaryl compound represented by general formula (5):

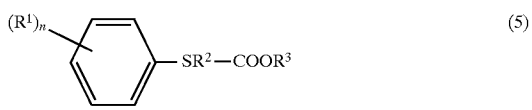

which process comprises reacting the above-mentioned alkalimetal salt of an arylmercaptan compound with a halogenofattyacid ester compound represented by general formula (4):

$$X^1R^2COOR^3 \qquad (4)$$

at pH 7–10; and a process for producing the above-mentioned alkoxycarbonylalkylthioaryl compound, which process comprises reacting the above-mentioned disulfide compound with the above-mentioned hydroxide of an alkali metal $M^1$ in the presence of the above-mentioned sulfur compound to obtain an alkali metal salt of an arylmercaptan compound, and reacting said alkali metal salt, without isolating it, with the above-mentioned halogenofatty acid ester compound under the same condition as mentioned above.

3 Claims, No Drawings

PROCESS FOR PRODUCTION OF THIOARYL COMPOUND

This is a Continuation of application Ser. No. 08/532,801 filed on Nov. 8, 1995, now U.S. Pat. No. 5,754,760, which was filed as International Application No. PCT/JP95/00455, filed Mar. 17, 1995.

TECHNICAL FIELD

The present invention relates to processes for producing alkoxycarbonylalkylthioaryl compounds useful as an intermediate for herbicide synthesis, and related compounds thereof.

BACKGROUND ART

A process for production of an arylmercaptan compound is known which comprises reducing an aryl disulfide compound with an iron powder or a zinc powder. This process, however, is troublesome in the disposal of the iron powder or zinc powder used. A process for production of an aryl mercaptan compound from a disulfide compound using an alkali hydroxide, is advantageous in that the process can be carried out under relatively mild reaction conditions. The process, however, has a drawback in that the yield of arylmercaptan compound (an intended product) is low because the product is partially oxidized to generate by-products such as arylsulfinic acid and the like; thus, the process has been unsuitable as an intermediate step for production of an alkoxycarbonylalkylthioaryl compound.

A 2,4-dihalo-5-methoxycarbonylthioaniline derivative obtained from 5,5'-(2,4-dihalogenoaniline) disulfide (which is an aryl disulfide compound above mentioned) represented by the following general formula:

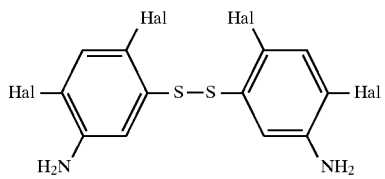

is unstable and cannot be isolated at a high yield. Thus, it has been difficult to produce, in industry, an intended alkoxycarbonylalkylthioaryl compound from a substituted aryldisulfide compound which is an expensive raw material.

The task to be achieved by the present invention is to provide industrial processes for producing a metal salt of an arylmercaptan compound and an alkoxycarbonylalkylthioaryl compound in an easy operation at a high yield.

In order to achieve the above task, the present inventors made a study hardly on a process for producing an alkoxycarbonylalkylthioaryl compound. As a result, the present inventors unexpectedly found out that by allowing a sulfur compound to be present in the reaction of an aryl disulfide compound with an alkali metal hydroxide, the aryl disulfide compound can be converted into an alkali metal salt of a corresponding arylmercaptan compound at a high yield, that by reacting said alkali metal salt with a halogenofatty acid ester compound at pH 7–10, said alkali metal salt can be converted into an alkoxycarbonylalkylthioaryl compound easily at a high yield, and that these reactions can be carried out continuously in the same reactor. The present invention has been completed based on the above findings.

DISCLOSURE OF THE INVENTION

The present invention provides:

a process for producing an alkali metal salt of an arylmercaptan compound, represented by general formula (3):

(wherein $R^1$s are each a hydrogen atom, a halogen atom, an amino group, an acylamino group, an alkyl group, an alkoxy group, a phenyl group, an alkylamino group, a dialkylamino group, a benzyl group or an acyl group; n is an integer of 1–5; when n is 2 or more, $R^1$s may be the same or different; $M^1$ is an alkali metal), which process comprises reacting a disulfide compound represented by general formula (1):

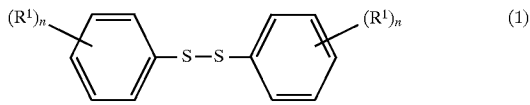

(wherein $R^1$s and n have the same definitions as given above) with a hydroxide of an alkali metal $M^1$ in the presence of a sulfur compound represented by general formula (2):

$$H_{(2-i)}S(M^1)_i \qquad (2)$$

(wherein $M^1$ has the same definition as given above, and i is an integer of 1 or 2);

a process for producing an alkoxycarbonylalkylthioaryl compound represented by general formula (5):

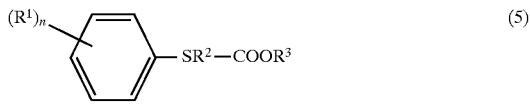

(wherein $R^1$s and n have the same definitions as given above; $R^2$ is an alkylene group; $R^3$ is an alkyl group), which process comprises reacting an alkali metal salt of an arylmercaptan compound, represented by general formula (3):

(wherein $R^1$s, n and $M^1$ have the same definitions as given above) with a halogenofatty acid ester compound represented by general formula (4):

$$X^1R^2COOR^3 \qquad (4)$$

(wherein $R^2$ and $R^3$ have the same definitions as given above, and $X^1$ is a halogen atom) at pH 7–10; and a process for producing an alkoxycarbonylalkylthioaryl compound represented by general formula (5):

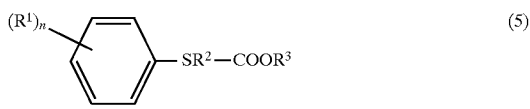

(wherein $R^1$s, n, $R^2$ and $R^3$ have the same definitions as given above), which process comprises reacting a disulfide compound represented by general formula (1):

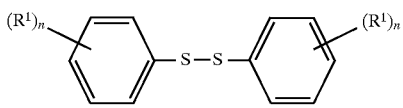 (1)

(wherein $R^1$s and n have the same definitions as given above) with a hydroxide of an alkali metal $M^1$ in the presence of a sulfur compound represented by general formula (2):

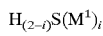 (2)

$H_{(2-i)}S(M^1)_i$ (wherein $M^1$ and i have the same definitions as given above) to obtain an alkali metal salt of an arylmercaptan compound, represented by general formula (3):

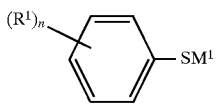 (3)

(wherein $R^1$s, n and $M^1$ have the same definitions as given above), and then reacting said salt, without isolating it, with a halogenofatty acid ester compound represented by general formula (4):

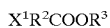

$X^1R^2COOR^3$ (4)

(wherein $R^2$, $R^3$ and $X^1$ have the same definitions as given above) at pH 7–10.

BEST MODE FOR CARRYING OUT THE INVENTION

The present invention is hereinafter described in detail in order.

Production of alkali metal salt of arylmercaptan compound

The disulfide compound represented by general formula (1), used in the present invention can be exemplified by those having, as each substituent $R^1$ of general formula (1), a hydrogen atom; a halogen atom, specifically a fluorine atom, a chlorine atom, a bromine atom or an iodine atom; an amino group; an acylamino group, specifically an acylamino group having 1–6 carbon atoms, more specifically an acylamino group wherein the acyl group is an acetyl group, a propionyl group, a butanoyl group, a pentanoyl group or a hexanoyl group; an alkyl group, specifically an alkyl group having 1–6 carbon atoms, more specifically a methyl group, an ethyl group, a propyl group, an isopropyl group, a butyl group, an isobutyl group, a tert-butyl group, a sec-butyl group, a pentyl group, an isopentyl group, a neopentyl group, a hexyl group or the like (in the present specification, "alkyl group" includes even a cycloalkyl group such as cyclohexyl group or the like); an alkoxyl group, specifically an alkoxyl group wherein the alkyl moiety bonding to the oxygen atom is the above-mentioned alkyl group; a phenyl group; an alkylamino group, specifically an alkylamino group wherein the alkyl moiety bonding to the nitrogen atom is the above-mentioned alkyl group; a dialkylamino group, specifically a dialkylamino group wherein the alkyl moieties bonding to the nitrogen atom are each the above-mentioned alkyl group; a benzyl group; an aromatic acyl group, specifically a benzoyl group; an aliphatic acyl group, specifically an aliphatic acyl group having 1–6 carbon atoms, more specifically an acetyl group, a propionyl group, a butanoyl group, a pentanoyl group or a hexanoyl group; or the like.

The n in the $(R^1)_n$ of the disulfide compound represented by the general formula (1) is an integer of 1–5. $(R^1)_n$ refers to that 1–5 substituents $R^1$s as mentioned above bond to a benzene ring. There is no particular restriction as to the bonding site of each substituent $R^1$. When n is 2 or more, the substituents $R^1$s may be the same or different.

A specific example of the disulfide compound includes one represented by general formula (6):

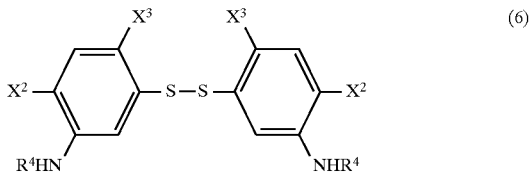 (6)

In the above disulfide compound, each $R^4$ is a hydrogen atom, or an acyl group having 1–6 carbon atoms, specifically an acetyl group, a propionyl group, a butanoyl group, a pentanoyl group, a hexanoyl group or the like; each $X^2$ and each $X^3$ are each a halogen atom, specifically a fluorine atom, a chlorine atom, a bromine atom or an iodine atom.

The alkali metal hydroxide usable in the present invention can be exemplified by potassium hydroxide, sodium hydroxide and lithium hydroxide. The alkali metal hydroxide may be a mixture of two or more kinds, if desired. The alkali metal hydroxide is used in the form of an aqueous solution containing generally 1–50% by weight, preferably 5–20% by weight of the alkali metal hydroxide. The amount of the alkali metal hydroxide used is 2 moles or more per mole of the disulfide compound, but is generally 2–20 moles, preferably 4–6 moles in view of the reaction rate, etc.

The sulfur compound of general formula (2), usable in the present invention includes, for example, potassium sulfide [a compound of general formula (2) wherein $M^1$=K and i=2], sodium sulfide [a compound of general formula (2) wherein $M^1$=Na and i=2], lithium sulfide [a compound of general formula (2) wherein $M^1$=Li and i=2], sodium hydrosulfide [a compound of general formula (2) wherein $M^1$=Na and i=1], potassium hydrosulfide [a compound of general formula (2) wherein M1=K and i=1], lithium hydrosulfide [a compound of general formula (2) wherein $M^1$=Li and i=1], and potassium sodium sulfide [a compound of general formula (2) wherein $M^1$=K and Na and i=2]. The sulfur compound may be used in admixture of two or more kinds, if desired.

The amount of the sulfur compound used is 0.1–0.9 mole, preferably 0.2–0.7 mole per mole of the disulfide compound. When the amount is less than the above range, the intended product has not a sufficiently improved stability in the reaction system; when the amount is -more than the above range, the resulting effect is not much different from when the amount is within the above range, which is disadvantageous in operation and economy.

In the present invention, the reaction of the disulfide compound with the alkali metal hydroxide is conducted generally in an aqueous solution containing said alkali metal hydroxide, generally at 10° C. to the reflux temperature of the reaction system, preferably at 30°–120° C., generally under atmospheric pressure. In the reaction, there is no restriction as to the addition order of raw materials, etc., and their addition can be made in any order. The alkali metal salt of an arylmercaptan compound, represented by general formula (3), which is a reaction product, can be obtained generally in the form of an aqueous solution thereof.

When the alkali metal $M^1$ in the hydroxide of an alkali metal $M^1$ and the alkali metal $M^1$ in the sulfur compound of general formula (2) are different, the resulting alkali metal salt of an arylmercaptan compound, represented by general formula (3) is a mixture of different alkali metal salts. This is no problem in the present invention.

In the present invention, an alcohol such as methanol, ethanol, propanol, isopropanol or the like may be added to the reaction system, if desired, in an amount of 0.1–2 liters, preferably 0.1–1 liter per mole of the disulfide compound. This addition has been found to make a reaction rate higher. After the completion of the reaction, by removing the alcohol for recovery by distillation or the like, the reaction product can be obtained in the form of, for example, an aqueous solution thereof.

Production of Alkoxycarbonylalkylthioaryl Compound

The alkali metal salt of an arylmercaptan compound, used in the present invention is represented by general formula (3). The salt is produced preferably by the present process described above.

The halogenofatty acid ester compound represented by general formula (4), usable in the present invention is an ester having a $X^1$—$R^2$ group ($X^1$ is a halogen atom and $R^2$ is an alkylene group), specifically a $C_{1-6}$ straight, branched or alicyclic monohalogeno alkyl group having one fluorine, chlorine, bromine or iodine atom, more specifically a monochloromethyl group, a 1-chloroethyl group, a 2-chloroethyl group, a 1-chloropropyl group, a 1-chloroisopropyl group, a 1-chlorobutyl group, a 1-chloroisobutyl group, a 1-chloro-tert-butyl group, a 1-chloro-sec-butyl group, a 1-chloropentyl group, a 1-chloroisopentyl group, a 1-chloroneopentyl group, a 1-chlorohexyl group, a 1-chlorocyclohexyl group; a monobromomethyl group, a 1-bromoethyl group, a 2-bromoethyl group, a 1-bromopropyl group, a 1-bromoiso propyl group, a 1-bromobutyl group, a 1-bromoisobutyl group, a 1-bromo-tert-butyl group, a 1-bromo-sec-butyl group, a 1-bromopentyl group, a 1-bromoisopentyl group, a 1-bromoneopentyl group, a 1-bromohexyl group, a 1-bromocyclohexyl group; a monoiodomethyl group, a 1-iodoethyl group, a 2-iodoethyl group, a 1-iodopropyl group, a 1-iodoisopropyl group, a 1-iodobutyl group, a 1-iodoisobutyl group, a 1-iodo-tert-butyl group, a 1-iodo-sec-butyl group, a 1-iodopentyl group, a 1-iodoisopentyl group, a 1-iodoneopentyl group, a 1-iodohexyl group, a 1-iodocyclohexyl group; a monofluoromethyl group, a 1-fluoroethyl group, a 2-fluoroethyl group, a 1-fluoropropyl group, a 1-fluoroisopropyl group, a 1-fluorobutyl group, a 1-fluoroisobutyl group, a 1-fluoro-tert-butyl group, a 1-fluoro-sec-butyl group, a 1-fluoropentyl group, a 1-fluoroisopentyl group, a 1-fluoroneopentyl group, a 1-fluorohexyl group (even a 1-fluorocyclohexyl group or the like is included as in the case of the alkyl group mentioned-above) or the like.

The $R^3$ in the halogenofatty acid ester compound is an alkyl group having 1–6 carbon atoms, specifically a methyl group, an ethyl group, a propyl group, an isopropyl group, a butyl group, an isobutyl group, a tert-butyl group, a sec-butyl group, a pentyl group, an isopentyl group, a neopentyl group, a hexyl group, a cyclohexyl group or the like.

In the present invention, the alkali metal salt of an arylmercaptan compound, of general formula (3) and the halogenofatty acid ester compound of general formula (4) are reacted preferably in a heterogeneous solvent consisting of water and an organic solvent which is substantially inert to the reaction of the two compounds and which has substantially no compatibility with water. The organic solvent which is substantially inert to the reaction and which has substantially no compatibility with water, usable in the reaction can be exemplified by aromatic hydrocarbons such as benzene, toluene, xylene, chlorobenzene, dichlorobenzene and the like; and aliphatic hydrocarbons such as pentane, hexane, cyclohexane, heptane and the like.

In the present invention, prior to the reaction with the halogenofatty acid ester compound of general formula (4), the aqueous solution of the alkali metal salt of an arylmercaptan compound, of general formula (3) is made weakly basic (i.e. pH 7–10) by the use of an alkali metal carbonate, an alkali metal bicarbonate, a tertiary amine and/or a mineral acid. The alkali metal carbonate and the alkali metal bicarbonate can be specifically exemplified by potassium carbonate, sodium carbonate, lithium carbonate, potassium bicarbonate, sodium bicarbonate and lithium bicarbonate. The tertiary amine can be exemplified by triethylamine. The alkali metal carbonate, the tertiary amine and the alkali metal bicarbonate may be used in admixture of two or more kinds, if desired. The mineral acid can be exemplified by hydrochloric acid, sulfuric acid, nitric acid and phosphoric acid.

The above pH control is generally conducted, in view of the easiness of operation, etc., by adding the alkali metal carbonate and/or the alkali metal bicarbonate in an amount of 1 mole or more, preferably 2–10 moles per mole of the alkali metal salt of an arylmercaptan compound and then adding an appropriate amount of the mineral acid to let a pH of 7–10, preferably 7–9. This pH control may be conducted using the mineral acid alone without using the alkali metal carbonate and/or the alkali metal bicarbonate, or the tertiary amine. In the pH control, the temperature of the aqueous solution of the alkali metal salt of an arylmercaptan compound, of general formula (3) is kept at 100° C. or below, preferably 30° C. or below.

In the present invention, the aqueous solution of the alkali metal salt of an arylmercaptan compound, having a pH controlled as above is mixed with the halogenofatty acid ester compound. The mixture is subjected to a reaction generally at 0°–100° C., preferably at 10°–50° C. generally under atmospheric pressure, whereby is obtained an intended compound, i.e. an alkoxycarbonylalkylthioaryl compound represented by general formula (5).

The amount of the halogenofatty acid ester compound used is 1 mole or more per mole of the alkali metal salt of an arylmercaptan compound but, in view of the reaction rate, etc., is generally 1–5 moles, preferably 1–2 moles.

Continuous Production of Alkoxycarbonylalkylthioaryl Compound

When the alkali metal salt of an arylmercaptan compound, of general formula (3) is, for example, unstable and its isolation is undesirable, said salt may be reacted, without being isolated, with the halogenofatty acid ester compound of general formula (4). In this way, for example, an alkoxycarbonylalkylthioaryl compound represented by general formula (7):

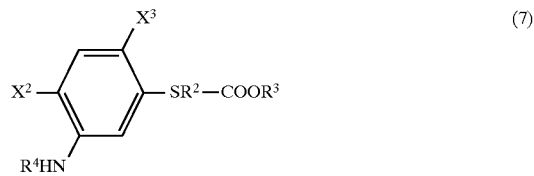

(wherein $R^2$, $R^3$, $R^4$, $X^2$ and $X^3$ have the same definitions as given above) can be produced from the disulfide compound represented by general formula (6).

The present invention is hereinafter described more specifically by way of Examples and Comparative Examples.

EXAMPLE 1

Into a 3 liter four-necked flask equipped with a stirrer and a condenser were fed 176.6 g (0.5 mole) of bis(5-amino-2-chloro-4-fluorophenyl) disulfide, 1,200 g (3.0 moles as sodium hydroxide) of a 10% aqueous sodium hydroxide solution, 300 ml of 2-propanol and 32.5 g (0.25 mole) of 60% sodium sulfide. The mixture was refluxed with heating and stirring for 2 hours to give rise to a reaction. After the completion of the reaction, 2-propanol was removed by distillation under reduced pressure. The distillation residue was cooled to room temperature to obtain an aqueous solution of sodium salt of 4-chloro-2-fluoro-5-mercaptoaniline. The solution was subjected to liquid chroma- tography, which indicated that the yield of said salt was 96.1% relative to bis(5-amino-2-chloro-4-fluorophenyl) disulfide.

Comparative Example 1

The procedure of Example 1 was repeated except that 60% sodium sulfide was not added, whereby was obtained an aqueous solution of sodium salt of 4-chloro-2-fluoro-5-mercapoaniline. The solution was subjected to liquid chromatography, which indicated that the yield of said salt was 61.6% relative to bis(5-amino-2-chloro-4-fluorophenyl) disulfide.

EXAMPLE 2

Into a 3 liter four-necked flask equipped with a stirrer, a thermometer and a condenser were fed the aqueous solution of sodium salt (of an amount corresponding to 1.0 mole) of 4-chloro-2-fluoro-5-mercaptoaniline, obtained in Example 1 and 106 g (1.0 mole) of sodium carbonate. While the mixture was kept at 30° C. or below, 35% hydrochloric acid was dropwise added thereto to control the pH of the mixture at 9. Thereto was added 1,000 ml of toluene, followed by dropwise addition of 153 g (1.0 mole) of methyl bromoacetate at 20° C. or below. The mixture was stirred at room temperature for 30 minutes. Then, the organic layer was taken out by the use of a separatory funnel, washed with water, and subjected to distillation for solvent removal to obtain 237.9 g of 4-chloro-2-fluoro-5-methoxycarbonylthioaniline.

The product was subjected to liquid chromatography, which indicated that the purity was 91.0% and the yield was 86.5%.

Comparative Example 2

The procedure of Example 2 was repeated except that the pH control by hydrochloric acid was made at 11, whereby was obtained 179.1 g of 4-chloro-2-fluoro-5-methoxycarbonylthioaniline. The product was subjected to liquid chromatography, which indicated that the purity was 78.3% and the yield was 56.2%.

EXAMPLE 3

Into a 3 liter four-necked flask equipped with a stirrer and a condenser were fed 176.6 g (0.5 mole) of bis(5-amino-2-chloro-4-fluorophenyl)disulfide, 1,200 g (3.0 moles as sodium hydroxide) of a 10% aqueous sodium hydroxide solution, 300 ml of 2-propanol and 32.5 g (0.25 mole) of 60% sodium sulfide. The mixture was refluxed with heating and stirring for 2 hours to give rise to a reaction. After the completion of the reaction, 2-propanol was removed by distillation under reduced pressure to obtain an aqueous solution of sodium salt of 4-chloro-2-fluoro-5-mercaptoaniline. Thereto was added 106 g (1.0 mole) of sodium carbonate. While the mixture was kept at 30° C. or below, 35% hydrochloric acid was dropwise added thereto to control the pH of the mixture at 9. Thereto was added 1,000 ml of toluene, followed by dropwise addition of 153 g (1.0 mole) of methyl bromoacetate at 20° C. or below. The mixture was stirred at room temperature for 30 minutes. Then, the organic layer was taken out by the use of a separatory funnel, washed with water, and subjected to distillation for solvent removal to obtain 227.8 g of 4-chloro-2-fluoro-5-methoxycarbonylthioaniline having a melting point of 56°–60° C. The product was subjected to liquid chromatography, which indicated that the purity was 91.5% and the yield was 83.5%.

EXAMPLES 4–7

The procedure of Example 3 was repeated except that the kind and/or addition amount of the sulfur compound was changed, to obtain 4-chloro-2-fluoro-5-methoxycarbonylthioaniline. The results are shown in Table 1.

TABLE 1

| | Examples | | | |
|---|---|---|---|---|
| | 4 | 5 | 6 | 7 |
| Sulfur compound | NaHS | NaHS | $Na_2S$ | $Na_2S$ |
| Addition amount (moles per mole of disulfide compound) | 0.7 | 0.3 | 0.3 | 0.2 |
| Yield | 89.9 | 84.6 | 84.2 | 80.8 |

Industrial Applicability

The present invention has made it possible to produce, in industry, an alkoxycarbonylalkylthioaryl compound at a high yield by an easy operation even when an expensive aryldisulfide compound is used as a raw material.

We claim:

1. A process for producing an alkali metal salt of an arylmercaptan compound, represented by general formula (3):

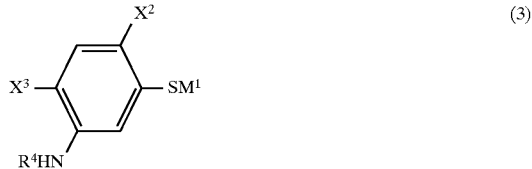

(wherein $R^4$ is a hydrogen atom or an acyl group; $X^3$ and $X^2$ are each a halogen atom; $M^1$ is an alkali metal), which process comprises reacting a disulfide compound represented by general formula (1):

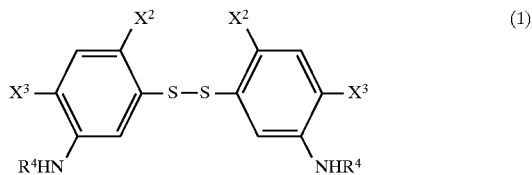

(wherein $R^4$, $X^3$ and $X^2$ have the same definitions as given above) with a hydroxide of an alkali metal $M^1$ in the presence of a sulfur compound represented by general formula (2):

(wherein $M^1$ has the same definition as given above, and i is an integer of 1 or 2).

2. A process according to claim 1, wherein an alcohol is added in the reaction of a disulfide compound with an alkali metal hydroxide in the presence of a sulfur compound.

3. A process for producing an alkoxycarbonylalkylthio-aryl compound represented by general formula (5):

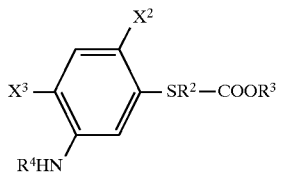 (5)

(wherein $R^4$ is a hydrogen atom or an acyl group; $X^3$ and $X^2$ are each a halogen atom; $R^2$ is an alkylene group; $R^3$ is an alkyl group), which process comprises reacting an alkali metal salt of an arylmercaptan compound, represented by general formula (3):

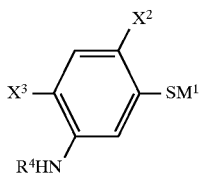 (3)

(wherein $R^4$, $X^3$ and $X^2$ have the same definitions as given above, and $M^1$ is an alkali metal) with a halogeno fatty acid ester compound represented by general formula (4):

$$X^1R^2COOR^3 \qquad (4)$$

(wherein $R^2$ and $R^3$ have the same definitions as given above, and $X^1$ is a halogen atom) at pH 7–10.

* * * * *